(12) United States Patent
Nakayama et al.

(10) Patent No.: US 7,456,959 B2
(45) Date of Patent: Nov. 25, 2008

(54) PARTICLE CLASSIFYING APPARATUS AND METHOD THEREOF

(75) Inventors: Atsushi Nakayama, Takasago (JP); Keisuke Tsutsumida, Kobe (JP)

(73) Assignee: Sysmex Corporation, Kobe-Shi (JP)

( * ) Notice: Subject to any disclaimer, the term of this patent is extended or adjusted under 35 U.S.C. 154(b) by 369 days.

(21) Appl. No.: 11/165,132

(22) Filed: Jun. 24, 2005

(65) Prior Publication Data

US 2006/0012787 A1 Jan. 19, 2006

(30) Foreign Application Priority Data

Jul. 15, 2004 (JP) ............................. 2004-208888

(51) Int. Cl.
*G01N 15/02* (2006.01)

(52) U.S. Cl. ...................................... 356/336; 356/337

(58) Field of Classification Search ............. 356/72–73, 356/317–318, 335–343, 442; 324/73.1
See application file for complete search history.

(56) References Cited

U.S. PATENT DOCUMENTS

| | | | |
|---|---|---|---|
| 4,263,508 A * | 4/1981 | Leary et al. | 250/358.1 |
| 4,612,614 A * | 9/1986 | Deindoerfer et al. | 356/335 |
| 5,719,666 A | 2/1998 | Fukuda et al. | |

* cited by examiner

*Primary Examiner*—Gregory J. Toatley, Jr.
*Assistant Examiner*—Tri T Ton
(74) *Attorney, Agent, or Firm*—Birch, Stewart, Kolasch & Birch, LLP

(57) ABSTRACT

A particle classifying apparatus is described, a representative one of which includes: a light source for irradiating light to a sample containing urine; a light-receiving device for receiving light from the sample irradiated with light; and means for classifying a first cast appearing in urine in the case of a disease from the other particles contained in the sample based upon an output from the light-receiving device.

17 Claims, 9 Drawing Sheets

[Fig. 1]
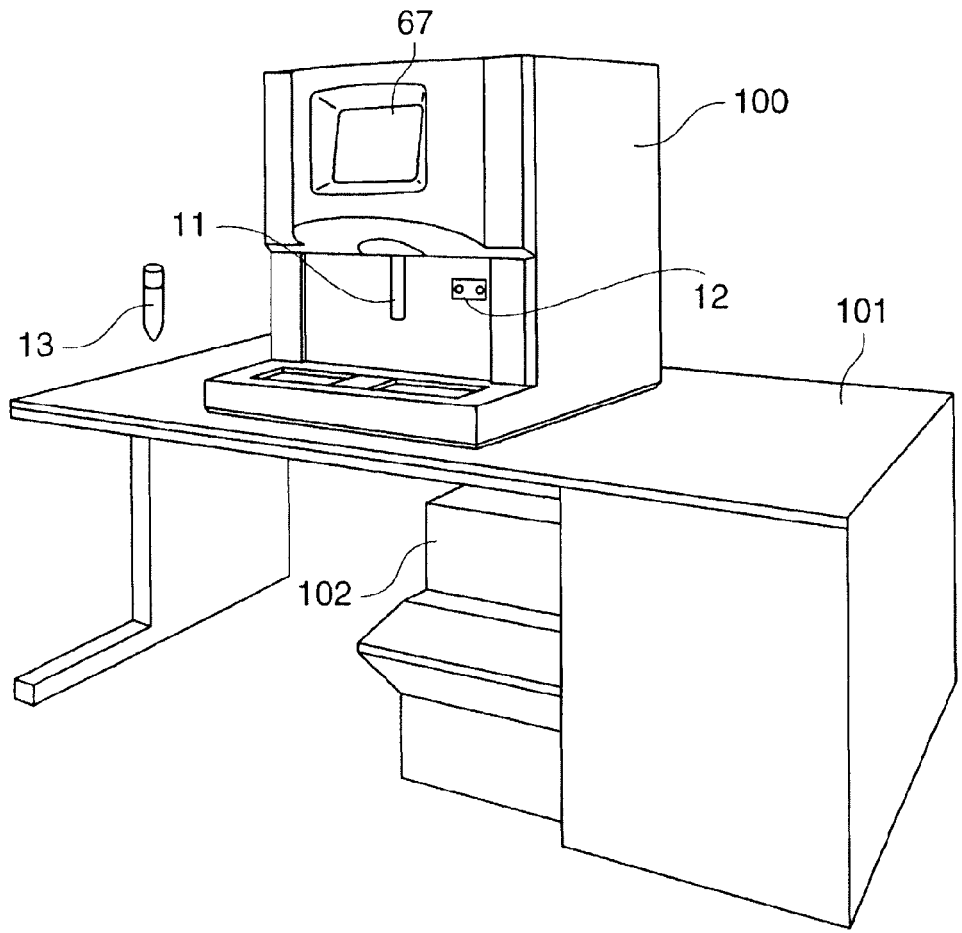
[Fig. 2]
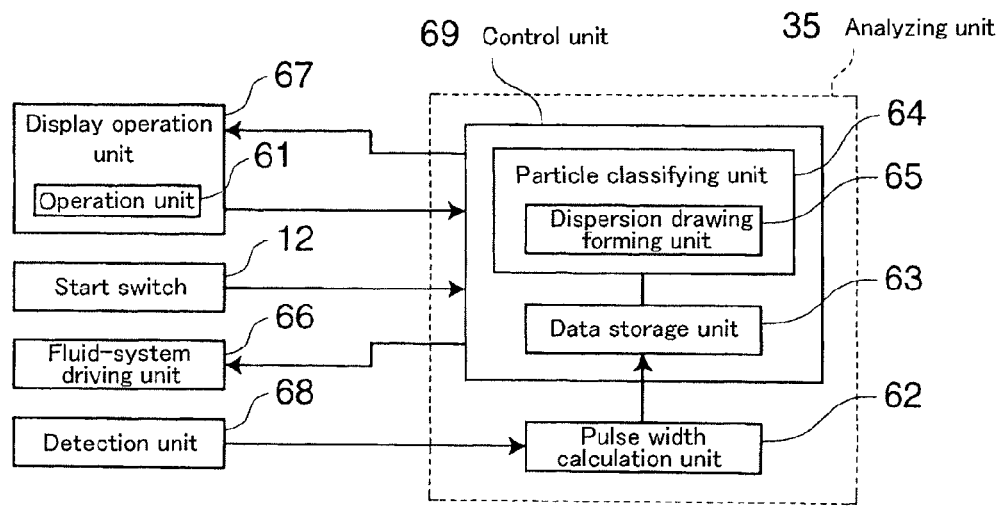

[Fig. 3]
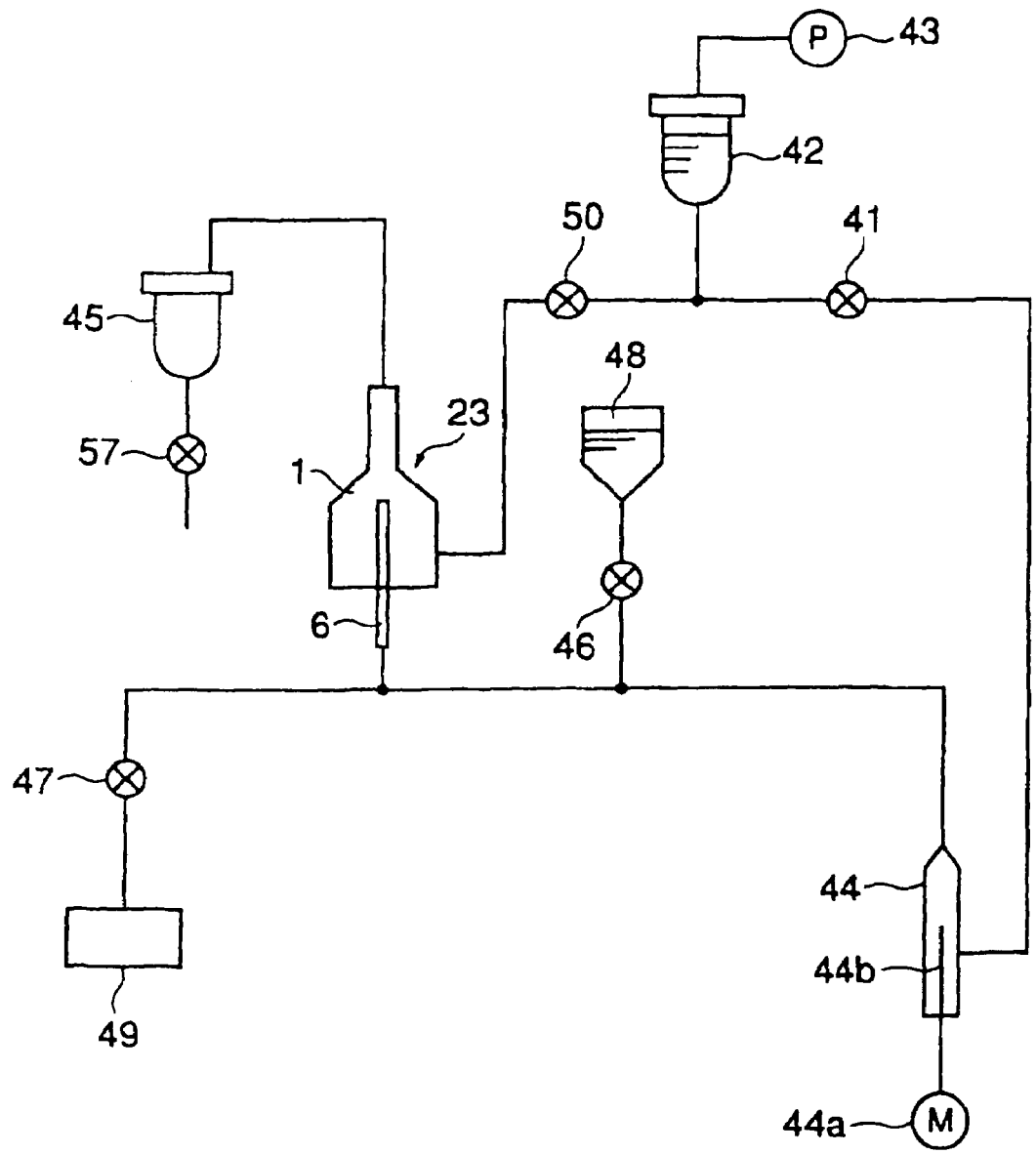

[Fig. 4]
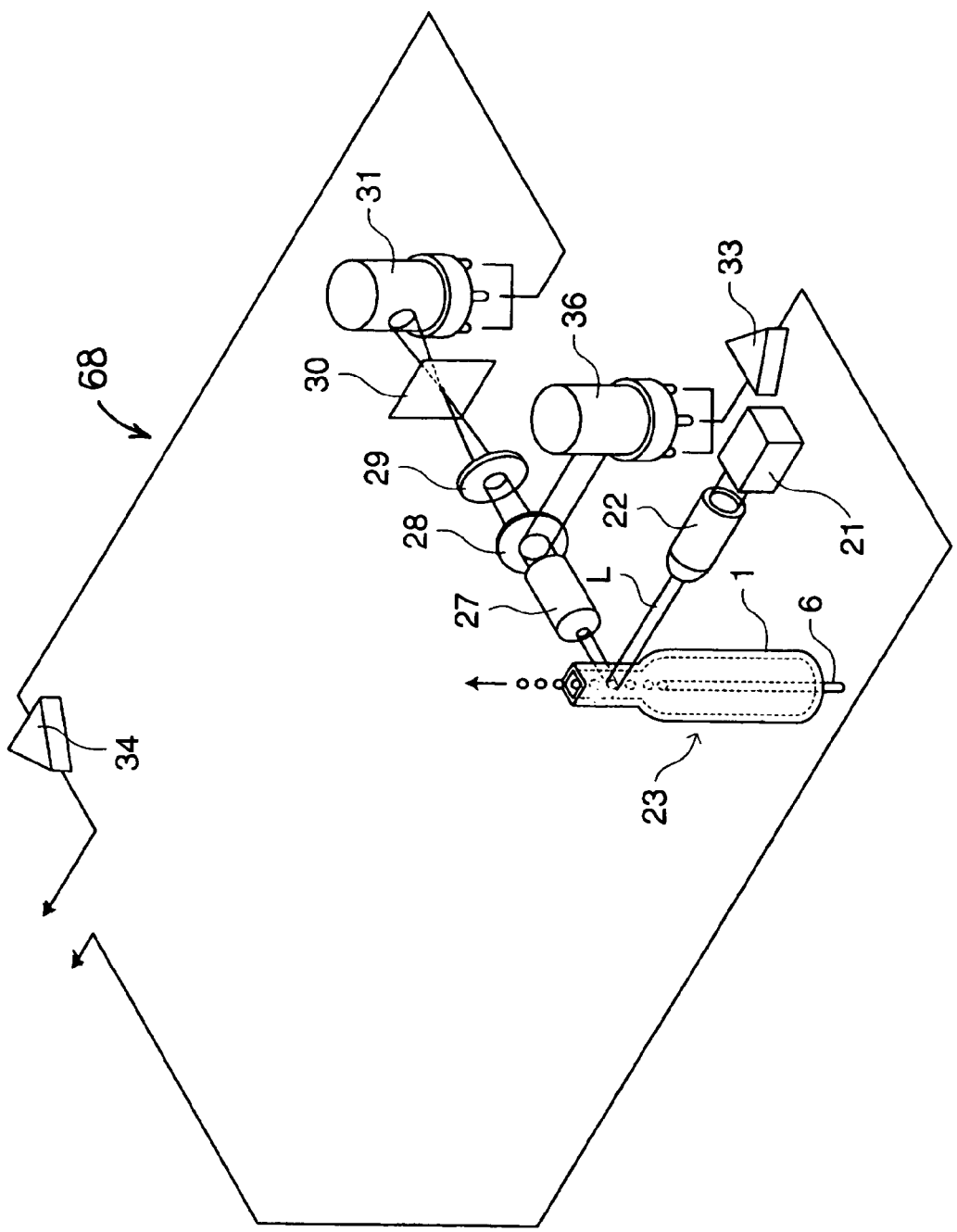

[Fig. 5]
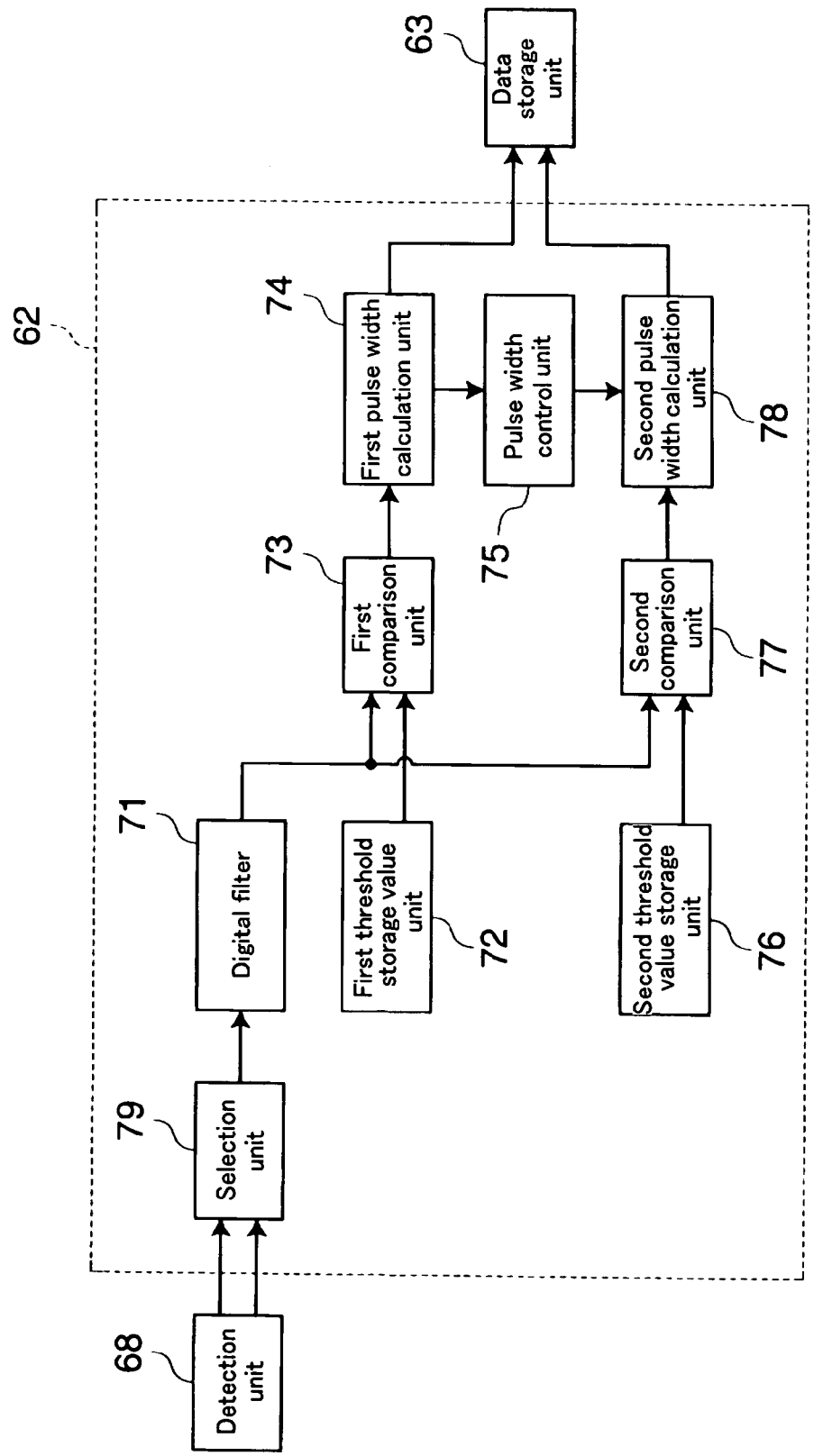

[Fig. 6]
(a)
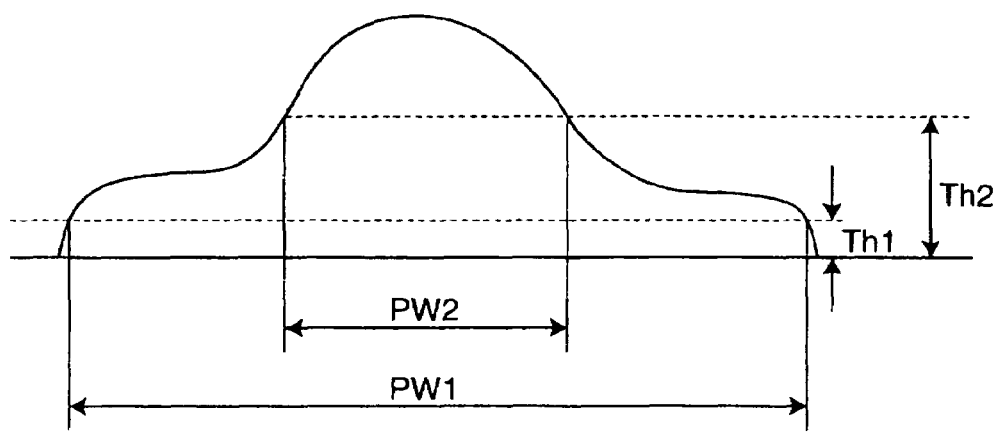
(b)
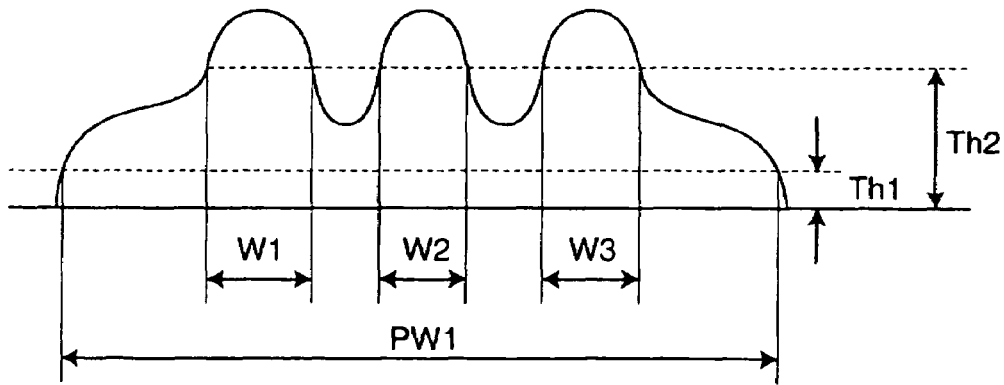

[Fig. 7]
(a)
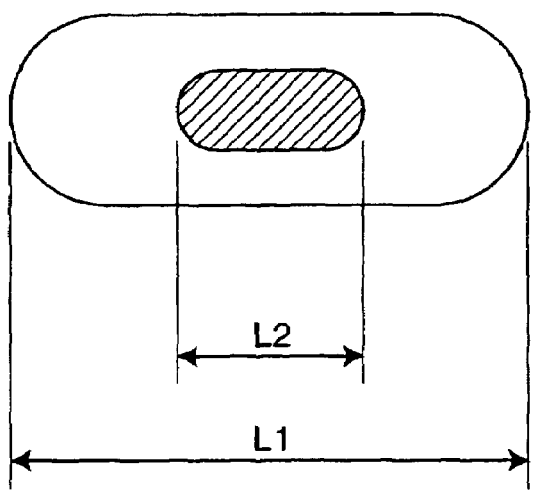
(b)
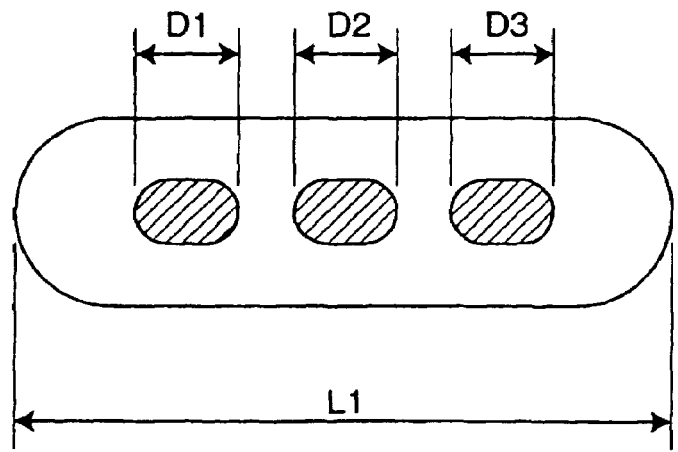

[Fig. 8]
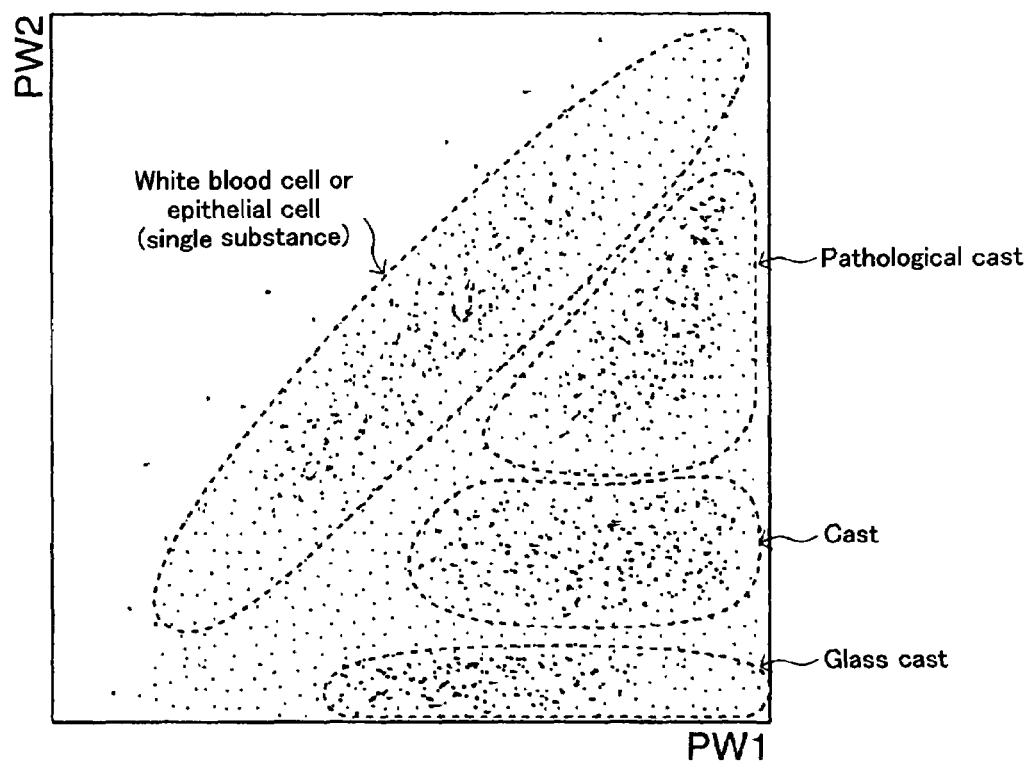

[Fig. 9]
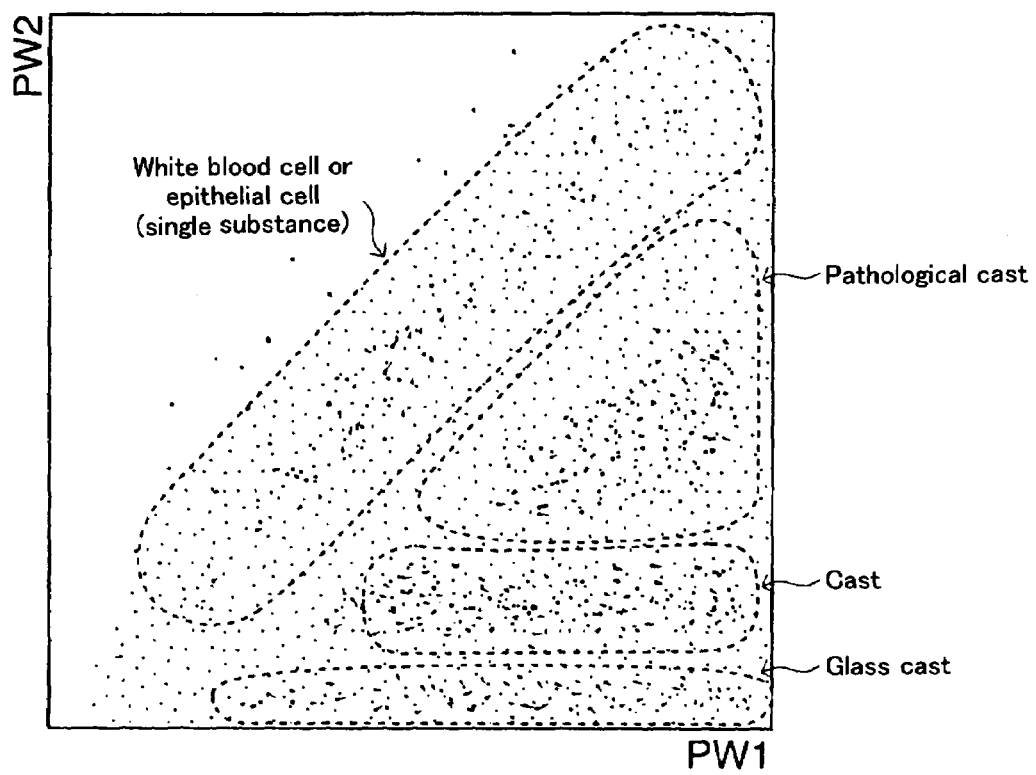

[Fig. 10]
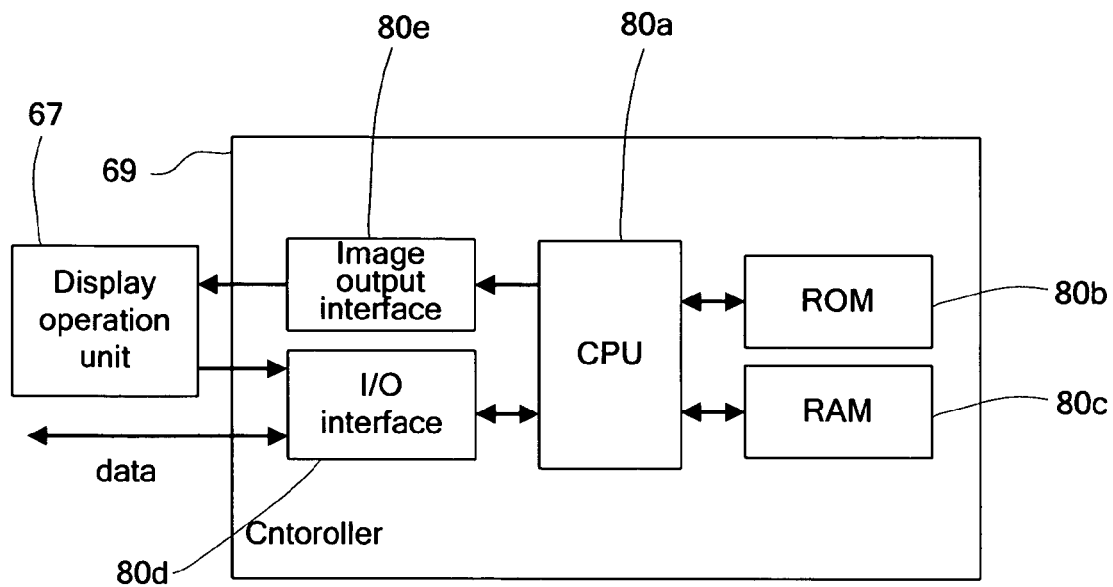
[Fig. 11]
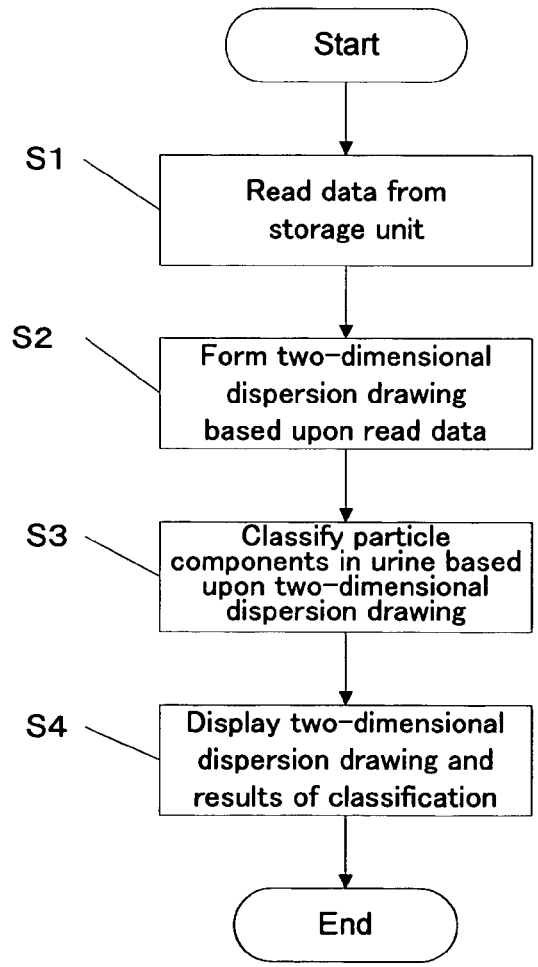

PARTICLE CLASSIFYING APPARATUS AND METHOD THEREOF

FIELD OF THE INVENTION

The present invention relates to a particle classifying apparatus and a method for such an apparatus, and more particularly, concerns an apparatus used for classifying particle components in urine.

BACKGROUND

Conventionally, particle components contained in urine have been analyzed so as to detect a disease in the kidney and the bladder. In the urine, cast, mucous cells, epithelial cells, white blood cell or the like are contained as particle components. The cast, which form one of the particle components, tend to appear not only in the case of a disease but also in a normal state, and the cast (cast appearing in the case of a disease) that appear in urine in the case of a disease contain more white blood cell and other cell components in comparison with cast (cast appearing in a normal state) that appear in a normal state.

With respect to the apparatus for analyzing the particle components in urine, for example, a particle analyzer disclosed in U.S. Pat. No. 5,719,666 has been known. The analyzer, disclosed in the above-mentioned patent gazette, can classify components, such as cast, mucous cells, epithelial cells and white blood cell. However, the above-mentioned analyzer cannot finely classify the cast into the cast appearing in the case of a disease and the cast appearing in a normal state.

SUMMARY

The present invention has been devised to solve the above-mentioned problems, and its objective is to provide a particle classifying apparatus capable of finely classifying cast and a method for such an apparatus.

In accordance with a first aspect of the present invention, the particle classifying apparatus is constituted by a light source for irradiating light to a sample containing urine; a light-receiving device for reciving light from the sample irradiated with the light; and a means that classifies a first cast appearing in urine in the case of a disease from the other particles contained in the sample based upon an output from the light-receiving device.

In accordance with a second aspect of the present invention, the particle classifying apparatus is constituted by a light source for irradiating light to a sample containing urine; a light-receiving device for reciving light from particles in the sample irradiated with light, and outputs a particle signal corresponding to the particles; and a means that classifies a first cast appearing in the urine in the case of a disease from the other particles contained in the sample based upon a first pulse width that indicates a period of time during which the particle signal exceeds a first threshold value and a second pulse width that indicates a period of time during which the particle signal exceeds a second threshold value that is greater than the first threshold value.

In accordance with a third aspect of the present invention, the particle classifying method is constituted by the following steps: a step of applying light to a sample containing urine; a step of receiving light from the sample irradiated with the light by using a light-receiving device; and a step of classifying a cast appearing in urine in the case of a disease from the other particles contained in the sample based upon an output from the light-receiving device.

BRIEF DESCRIPTION OF THE DRAWINGS

FIG. 1 is a perspective view that shows an entire external structure of an analyzer for particle components in urine in accordance with one embodiment of the present invention.

FIG. 2 is a block diagram that shows an essential portion of the analyzer shown in FIG. 1.

FIG. 3 is a system diagram that shows a fluid system of the analyzer shown in FIG. 1.

FIG. 4 is a perspective view that shows a detection unit of the analyzer shown in FIG. 1.

FIG. 5 is a block diagram that shows a pulse width calculation unit of the analyzer shown in FIG. 1.

FIG. 6 is a waveform drawing of electric signals of the analyzer shown in FIG. 1.

FIG. 7 is an explanatory drawing that indicates a cast and the contents thereof.

FIG. 8 is an example of a dispersion drawing that is formed by the analyzer shown in FIG. 1.

FIG. 9 is an example of a dispersion drawing that is formed by the analyzer shown in FIG. 1.

FIG. 10 is a block diagram that shows a hardware structure of a control unit shown in FIG. 2.

FIG. 11 is a flow chart that explains a classifying flow of particle components in urine relating to processes in the control unit shown in FIG. 10.

DETAILED DESCRIPTION OF THE PREFERRED EMBODIMENT

The preferred embodiments of the present invention will be explained below with reference to the drawings. In the following embodiments, for example, an analyzer for particle components in urine will be explained as the particle classifying apparatus in accordance with the present invention.

FIG. 1 is a perspective view that shows an entire external structure of an analyzer for particle components in urine in accordance with one embodiment of the present invention. FIG. 2 is a block diagram that explains an essential portion of the analyzer for particle components in urine in accordance with the embodiment shown in FIG. 1. FIG. 3 is a system diagram that explains a fluid system of the analyzer for particle components in urine in accordance with the embodiment shown in FIG. 1. FIG. 4 is a perspective view that explains a structure of a detection unit of the analyzer for particle components in urine in accordance with the embodiment shown in FIG. 1. FIG. 5 is a block diagram that explains a structure of a pulse width calculation unit to be used in the analyzer for particle components in urine in accordance with the embodiment shown in FIG. 1. FIG. 10 is a block diagram that shows a hardware structure of a control unit 69 shown in FIG. 2.

Structure of Analyzer for Particle Components in Urine

Referring to FIGS. 1 to 5 and FIG. 10, the following description will explain a structure of an analyzer for particle components in urine in accordance with one embodiment of the present invention.

As shown in FIG. 1, an analyzer for particle components in urine in accordance with the present embodiment, which is provided with an apparatus main body 100, a table 101 and a power source 102 that includes a power supply and an air pressure supply, has functions for classifying particle components in a urine sample in a specimen container 13 into red blood cell, white blood cell, epithelial cells, cast and bacteria.

Moreover, a display operation unit 67 made of a liquid crystal screen is placed on the upper portion of the front face of the apparatus main body 100. Various pieces of information, such as the results of classification of a urine sample and various setting values, are displayed on the display operation unit 67. The display operation unit 67 also functions as a touch panel, and also serves as an operation unit for operating the apparatus. More specifically, various settings relating to measurements of the urine sample and operation keys used for selecting various functions are displayed on the liquid crystal screen of the display operation unit 67 so that the user is allowed to carry out operations, such as various settings and selections of various functions, by touching the operation keys on the liquid crystal screen. A suction pipette 11 used for sucking urine from the specimen container 13 is placed in the center of the front face of the apparatus main body 100. Moreover, a start switch 12 is placed on the right side in the center of the front face of the apparatus.

Referring to FIGS. 2 to 4 and FIG. 10, the following description will further describe the analyzer for particle components in urine in detail.

As shown in FIG. 2, the analyzer for particle components in urine is provided with an analyzing unit 35. The analyzing unit 35 is provided with a control unit 69 and a pulse width calculation unit 62. The control unit 69 is provided with a particle classifying unit 64 including a dispersion drawing forming unit 65, and a data storage unit 63. The control unit 69, which receives outputs from the operation unit 61 and the start switch 12, controls a fluid-system driving unit 66 and a detection unit 68. Moreover, the pulse width calculation unit 62, which receives an output from the detection unit 68, calculates the pulse width. The control unit 69 stores the data of the calculated pulse width in the data storage unit 63, and the particle classifying unit 64 forms a dispersion drawing in the dispersion drawing forming unit 65 based upon the pulse width data so that particle components in urine are classified. The control unit 69 is constituted by microcomputers including a CPU, ROM, RAM or the like. The data storage unit 63 is constituted by a memory such as a RAM.

Referring to FIG. 10, the structure of the control unit 69 is further explained. The control unit 69 is provided with a CPU 80a, a ROM 80b, a RAM 80c, an input/output (I/O) interface 80d and an image-output interface 80e. The ROM 80b stores an operating system, a control program used for controlling operations of the apparatus, data required for running the control program, an application program used for classifying particle components in urine, which will be described later, and data required for executing the application program. The CPU 80a is capable of loading the control program or the application program into the RAM 80c so as to be run, or directly runs the program through the ROM 80b. Thus, the resulting data after the processes by the CPU 80a are transmitted to the respective units of the apparatus through the input/output interface 80d, and data required for the processes of the CPU 80a are received from the respective units of the apparatus through the input/output interface 80d. By running the control program, the CPU 80a can control the fluid-system driving unit 66 of the analyzer for particle components in urine, which will be described later. Moreover, by executing the application program, the CPU 80a forms a two-dimensional dispersion drawing, which will be described later, so that the particle components in urine are classified, and allows the display operation unit 67 to display the results.

The analyzer for particle components in urine is also provided with a fluid system as shown in FIG. 3. This fluid system is constituted by a sheath flow cell 23 containing a cell 1 and a nozzle 6, a fixed-amount syringe 44 that is connected to the nozzle 6, a motor 44a that drives the piston 44b of the fixed-amount syringe 44, a reaction chamber 48 that is connected to the nozzle 6 through an electromagnetic valve 46, a sheath liquid chamber 42 that is connected to the cell 1 through an electromagnetic valve 50 and is also connected to the fixed-amount syringe 44 through an electromagnetic valve 41, a pressure device 43 that applies a positive pressure to the sheath liquid chamber 42, a suction device 49 that is connected to the nozzle 6 through an electromagnetic valve 47, a waste chamber 45 that is connected to the cell 1, and an electromagnetic valve 57 that is used for discharging the waste from the waste chamber 45. Here, the motor 44a, the electromagnetic valves 41, 46 and 47, the pressure device 43 and the suction device 49 constitute the fluid-system driving unit 66 shown in FIG. 2.

More specifically, the detection unit 68 shown in FIG. 2 has a structure shown in FIG. 4. In other words, the detection unit 68 is provided with a laser diode 21 and a collimate lens 22 used for illuminating an orifice section of the sheath flow cell 23, a condenser lens 27, a dichroic mirror 28 and a photomultiplier tube (hereinafter, referred to as photomultiplier) 36 that are used for detecting side scattered light from particles and a filter 29, a pin-hole plate 30 and a photomultiplier 31 that are used for detecting side fluorescent light from the particles. Moreover, amplifiers 33 or 34, which respectively amplify signals respectively outputted from the photomultipliers 36 and 31, and input the resulting signals to the selection unit 79 (FIG. 5), are also installed.

More specifically, the pulse width calculation unit 62 shown in FIG. 2 has a structure shown in FIG. 5. In other words, the pulse width calculation unit 62 is provided with a selection unit 79 that selects either of two output signals (output signals from the amplifiers 33 and 34) from the detection unit 68 (FIG. 4), and outputs the resulting signal, a digital filter 71 that filters the output of the selection unit 79, first and second threshold-value storage units 72 and 76, first and second comparison units 73 and 77 that respectively output periods that are greater than the first and second threshold values of the output of the digital filter 71 as pulse waves, first and second pulse width calculation units 74 and 78 that calculate pulse widths from the output pulses of the first and second comparison units 73 and 77, and a pulse-width control unit 75, which allows the pulse-width calculating operations of the second pulse width calculation unit 78, only within a period in which the output of the digital filter 71 is greater than the first threshold value, that is, only during a period in which the first pulse width calculation unit 74 is in operation based upon the output of the first comparison unit. Moreover, the pulse-width calculation unit 74 is designed so as to output an operation signal to the pulse-width control unit 75 during its operation. Here, the selection unit 79 is constituted by analog switches, the first and second threshold value storage units 72 and 76 are constituted by resistors, the first and second comparison units 73 and 77 are constituted by comparators, the first and second pulse width calculation units 74 and 78 are constituted by counters, and the pulse width control unit 75 is constituted by gates, respectively.

Operations of the Analyzer for Particle Components in Urine

Referring to FIGS. 1 to 5 and FIGS. 6 to 9, the following description will explain the operations of the analyzer for particle components in urine in accordance with the present embodiment. First, the user inserts the suction pipette 11 shown in FIG. 1 into the specimen container 13, and presses the start switch 12. Thus, urine inside the specimen container 13 is sucked through the suction pipette 11, and subjected to a fluorescent-dyeing process, and after having been diluted, the resulting urine is transferred to the reaction chamber 48 (see FIG. 3). In parallel with the transferring process of the urine, respective operations of the fluid system shown in FIG. 3 are carried out.

In FIG. 3, first, a washing process is carried out. In this washing process, first, the valves 41 and 50 are opened so that a sheath liquid is delivered from the sheath liquid chamber 42 storage the sheath liquid by a pressure P that is applied from the pressure device 43, and discharged into the waste chamber 45 through the valve 41, the fixed-amount syringe 44 and the nozzle 6, and also discharged into the waste chamber 45 through the valve 50 and the cell 1, and after a lapse of a predetermined period of time, the valves 41 and 50 are closed. Consequently, the fixed-amount syringe 44, the nozzle 6, the cell 1 and the routes thereof are washed by the sheath liquid.

Next, measuring processes are carried out. In these processes, first, the valves 46 and 47 are opened, and urine that has been treated by a reagent, that is, a sample fluid is sucked from the reaction chamber 48 preserving the sample fluid by a negative pressure of the suction device 49 so that, when the path between the valve 46 and the nozzle 6 has been filled with the sample fluid, the valves 46 and 47 are closed. Next, when the valve 50 is opened, the sheath liquid is delivered from the sheath liquid chamber 42 to the cell 1 by a pressure of the pressure device 43, and discharged into the waste chamber 45.

Next, when the valve 41 is opened, the pressure P applied from the pressure device 43 is also transmitted to the tip of the nozzle 6 through the fixed-amount syringe 44 so that at the tip of the nozzle 6, the pressure of the sheath liquid outside the nozzle is balanced with the pressure of the sample fluid inside the nozzle. Therefore, when the piston 44b of the fixed-amount syringe 44 is driven by the motor 44a in this state, the sample fluid, located between the valve 46 and the nozzle 6, is smoothly discharged from the nozzle 6 to the orifice section, and thinly narrowed by the sheath liquid and allowed to pass through the orifice section, and then discharged into the waste chamber 45 together with the sheath liquid.

Upon completion of the driving operation of the piston 44b of the fixed-amount syringe 44, the measuring processes are completed.

Next, the motor 44a is reversely rotated so that the piston 44b is pulled back, and the fixed-amount syringe 44 is returned to the initial state, and since the valves 41 and 50 are maintained in the opened state during this period of time, the above-mentioned washing process is carried out so as to prepare for the next measuring processes. Here, the valve 57 is opened and closed on demand so as to discharge the waste from the waste chamber 45.

Moreover, in the above-mentioned measuring processes, in the detection unit 68 shown in FIG. 4, a light beam, released from the laser diode 21, is directed to the orifice section of the sheath flow cell 23 through the collimate lens 22.

With respect to side scattered light and side fluorescent light emitted from particles in the sample fluid passing through the orifice section, the side scattered light is made incident on the photomultiplier 36 through the condenser lens 27 and the dichroic mirror 28, while the side fluorescent light is made incident on the photomultiplier 31 through the condenser lens 27, the dichroic mirror 28, the filter 29 and the pin-hole plate 30.

A side scattered light signal released from the photomultiplier 36 and a side fluorescent light signal released from the photomultiplier 31 are respectively amplified by amplifiers 33 and 34, and inputted to the pulse width calculation unit 62 shown in FIG. 5.

The particle components in urine that are subjects to be classified in the present embodiment include cast, glass cast, white blood cell, red blood cell, bacteria, epithelial cells (single substance) or the like, and, in particular, since a pathologic cast contains a number of contents, the pathologic cast that appears in the case of a disease can be classified from cast that also appear during a normal state, depending on the number of the contents. For example, glass cast containing no contents and cast, each containing one or two contents, are classified into cast that appear during a normal state, while cast, each containing three or more contents, are classified into the pathologic cast that appear in the case of a disease. Here, those cast, each containing three or more white blood cell, are referred to as white blood corpuscle cast, and those cast, each containing three or more red blood cell, are referred to as red blood corpuscle cast. FIG. 7(a) is a top view of a cast of size L1, which contains one content (white blood corpuscle) of size L2, and FIG. 7(b) is a top view of a cast of size L1, which contains three contents of respective sizes of D1, D2 and D3. The electric signal waveforms (output waveforms of amplifier 34 or 33 in FIG. 4) of the side fluorescent light or the side scattered light of these cast are respectively indicated by FIG. 6(a) and FIG. 6(b). In other words, a pulse width PW1 corresponding to a portion greater than the first threshold value Th1 of the waveform of FIG. 6(a) is directly proportional to size L1 of the cast of FIG. 7(a), and a pulse width PW2 corresponding to a portion greater than the second threshold value Th2 is directly proportional to size L2 of the content of FIG. 7(a). Moreover, a pulse width PW1 corresponding to a portion greater than the first threshold value Th1 of the waveform of FIG. 6(b) is directly proportional to size L1 of the cast of FIG. 7(b), and pulse widths W1, W2 and W3 corresponding to portions greater than the second threshold value Th2 are directly proportional to sizes D1, D2 and D3 of the three contents of FIG. 7(b), respectively.

In the pulse width calculation unit 62 shown in FIG. 5, either one of signals obtained from the amplifiers 34 and 33 of the detection unit 68 of FIG. 4 is selected by the selection unit 79 (as to which of them should be selected, a determination is preliminarily set in the operation unit 61). The selected waveform is filtered by the digital filter 71, and inputted to the first and second comparators 73 and 77 so that the resulting waveforms are respectively compared with the first and second threshold values Th1 and Th2 outputted by the first and second threshold value storage units 72 and 76. Based upon the results of comparisons, the first and second pulse width calculation units 74 and 78 calculate the respective pulse widths.

In other words, when the output signal waveform of the digital filter 71 has a signal waveform shown in FIG. 6(a), the first and second pulse width calculation units 74 and 78 respectively calculate the first pulse width PW1 corresponding to the first threshold value Th1 and the second pulse width PW2 corresponding to the second threshold value Th2 that is greater than the first threshold value Th1. Moreover, when, as shown in FIG. 6(b), one signal waveform has a plurality of pulse widths W1, W2 and W3 corresponding to the second threshold value Th2, the second pulse width calculation unit 78 calculates a total sum of a plurality of the pulse widths, that is, (W1+W2+W3), as the second pulse width PW2, by the instruction of the pulse width control unit 75. The data, such as the first and second pulse widths PW1 and PW2, thus calculated, are stored in the data storage unit 63 shown in FIG. 2.

The dispersion drawing forming unit 65 of the particle classifying unit 64 shown in FIG. 2 reads data from the data storage unit 63, and forms a dispersion drawing based upon the first and second pulse widths PW1 and PW2 to classify the particles, and displays the results thereof on the display operation unit 67.

Referring to a flow chart shown in FIG. 11, the following description will explain the classifying flow of particle components in urine by the control unit 69 of the analyzer for particle components in urine. First, at step S1, a CPU 80a of the control unit 69 in the analyzer for particle components in urine reads the first pulse width PW1 and the second pulse width PW2 calculated by the pulse width calculation unit 62 from the RAM 80c (data storage unit 63). Next, at step S2, based upon the first pulse width PW1 and the second pulse width PW2 thus read, the CPU 80a forms a two-dimensional dispersion drawing. Next, at step S3, as shown in FIGS. 8 and 9, based upon the resulting two-dimensional dispersion drawing, the CPU 80a classifies particle components in urine into cast and the other components (white blood cell or epithelial cells (single substance)), and then finely classifies the cast into pathological cast, cast and glass cast. Next, at step S4, the CPU 80a displays the results of classifications (see FIGS. 8 and 9) of the particle components in urine together with the two-dimensional dispersion drawing on the display operation unit 67; thus, the processes of the classifying flow of the particle components in urine are completed.

Example of Measurements by the Analyzer for Particle Components in Urine

The following description will discuss an example of measurements carried out by this analyzer for particle components in urine. Human urine was used as a specimen; an aqueous solution containing HEPES, NaCl, EDTA-3K and NaOH was used as a diluent; an ethylene glycol solution containing a dye "NK-529" made by Nippon Kanko K. K. was used as a dyeing solution; and a Bactsheath MSE-900A made by Sysmex Corporation was used as the sheath liquid. Then, measurements were carried out, and FIGS. 8 and 9 show an example of a two-dimensional dispersion drawing, which has been formed by the dispersion drawing forming unit 65, and is displayed on the display operation unit 67.

FIG. 8 is a graph in which the pulse widths PW1 and PW2 of a side fluorescent light signal outputted from the photomultiplier 31 of FIG. 4 are respectively plotted on the X-axis and Y-axis, and FIG. 9 is a graph in which the pulse widths PW1 and PW2 of a side scattered light signal outputted from the photomultiplier 36 of FIG. 4 are respectively plotted on the X-axis and Y-axis.

FIGS. 8 and 9 indicate that particle components contained in urine can be clearly classified into white blood cell or epithelial cells (single substance), pathological cast that appear in the case of a disease (cast, each containing three or more contents), cast that appear in a normal state (cast, each containing one to two contents) and glass cast (cast containing no contents). Moreover, as indicated by two-dimensional dispersion drawings shown in FIGS. 8 and 9, the particle components contained in urine are classified by using demarcation lines.

In the above-mentioned embodiment, when a single electric signal waveform has a plurality of pulse widths corresponding to the second threshold value, the pulse width calculation unit calculates the total sum of a plurality of the pulse widths as the second pulse width so that, with respect to the pulse widths corresponding to a pathological cast, that is, a cast containing a plurality of contents, the total sum is calculated as the second pulse width. Therefore, since the second pulse width of the pathological cast becomes greater in comparison with the cast also observed in a normal state, it becomes possible to finely classify the cast into those that also appear in a normal state and those pathological cast.

In the above-mentioned embodiment, the particle components contained in urine are displayed by using demarcation lines on the two-dimensional dispersion drawing so as to be recognized; however, the colors of dots plotted on the two-dimensional dispersion drawing may be made coincident with the particle components to be classified. For example, dots corresponding to white blood cell or epithelial cells (single substance) may be displayed as blue dots, dots corresponding to pathological cast (cast that appear in the case of a disease) may be displayed as red dots, cast (cast that appear in a normal state) may be displayed as yellow dots, and glass cast (that contain no contents, and appear in a normal state) may be displayed as green dots.

In the above-mentioned embodiment, the pulse width has been calculated by using the pulse-width calculation unit 62 having an electric circuit configuration; however, the pulse width may be calculated on a software basis by using the control unit 69 constituted by microcomputers.

In the above-mentioned embodiment, the pulse width is calculated by using side fluorescent light or side scattered light emitted from particles so that cast are classified; however, the pulse width may be calculated by using high-angle scattered light emitted from particles so as to classify cast.

In the above-mentioned embodiment, as shown in FIG. 5, side scattered light from particles in urine is detected by a photomultiplier tube 36 from the orifice section of the sheath flow cell 23 illuminated by the laser diode 21, and side fluorescent light from the particles is detected by a photomultiplier tube 31. Based upon the detected signals, the particles are classified. In place of this mode, an image-pickup element such as a CCD may be placed on the light axis of a laser diode 21 with the orifice section of the sheath flow cell 23 being interpolated in between, and by analyzing a cast image picked up by the image-pickup element, the cast may be classified into pathological cast (cast that appear in the case of a disease), cast (cast that appear in a normal state) and glass cast (cast that contain no contents, and appear in a normal state).

In the above-mentioned embodiment, the two-dimensional dispersion drawing is formed based upon the first and second pulse widths so that the particles are classified, and the results are displayed; however, after classifying the particles based upon the first and second pulse widths, the two-dimensional dispersion drawing is formed so that the results of classifying processes may be displayed.

What is claimed is:

1. A particle classifying apparatus comprising:
   a light source for irradiating light to a sample containing urine;
   a light-receiving device for receiving light from the sample irradiated with light; and
   means for classifying a first cast appearing in urine in the case of a disease from other particles contained in the sample based upon an output from the light-receiving device,
   wherein the first cast contains three or more particle-shaped contents, and the other particles contain a second cast containing one or two particle-shaped contents.

2. The particle classifying apparatus according to claim 1, wherein the classifying means classifies the first cast and the second cast.

3. The particle classifying apparatus according to claim 2, wherein the classifying means classifies the first cast, the second cast and a glass cast.

4. The particle classifying apparatus according to claim 1, wherein the light-receiving device receives scattered light or fluorescent light derived from particles contained in the sample, and classifies the first cast based upon the output of the light-receiving device that corresponds to the scattered light or the fluorescent light.

5. The particle classifying apparatus according to claim 1, wherein: the light-receiving device is a capturing element that captures an image of particles contained in the sample, and the classifying means classifies the cast by analyzing the captured image.

6. A particle classifying method comprising the steps of:
applying light to a sample containing urine;
receiving light from the sample irradiated with light by using a light-receiving device; and
classifying a first cast appearing in urine in the case of a disease from other particles contained in the sample based upon an output from the light-receiving device,
wherein the first cast contains three or more particle-shaped contents, and the other particles contain a second cast containing one or two particle-shaped contents.

7. The particle classifying method according to claim 6, wherein: the light-receiving step receives scattered light or fluorescent light derived from particles contained in the sample from a light-receiving device, and the classifying step classifies the cast based upon the output of the light-receiving device corresponding to the scattered light or the fluorescent light.

8. The particle classifying method according to claim 6, wherein: the light-receiving step receives light from the particles in the sample irradiated with light, and the classifying step classifies the cast based upon the first pulse width that indicates a period of time during which the particle signal corresponding to particles exceeds the first threshold value and the second pulse width that indicates a period of time during which the particle signal exceeds a second threshold value that is greater than the first threshold value, outputted from the light-receiving device.

9. The particle classifying method according to claim 6, wherein the light-receiving device is a capturing element that captures an image of particles contained in the sample, and the classifying step classifies the cast by analyzing the captured image.

10. A particle classifying apparatus comprising:
a light source for irradiating light to a sample containing urine;
a light-receiving device for receiving light from particles in the sample irradiated with light, and outputting a particle signal corresponding to the particles; and
a classifier for obtaining a sum of pulse widths that indicates a period of time of the particle signal which corresponds to particle-shaped contents contained in cast, and for classifying cast into pathological cast and normal cast based on the obtained sum with respect to each the casts,
wherein the pathological cast contains three or more particle-shaped contents, and the normal cast contains one or two particle-shaped contents.

11. The particle classifying apparatus according to claim 10, wherein the light-receiving device receives fluorescent light from the particles, and the pulse width is a pulse width of the fluorescent light from the particle-shaped contents contained in the casts.

12. The particle classifying apparatus according to claim 10, wherein the light-receiving device receives scattered light from the particles, and the pulse width is a pulse width of the scattered light from the particle-shaped contents contained in the casts.

13. A particle classifying apparatus comprising:
a light source for irradiating light to a sample containing urine;
a light-receiving device for receiving light from particles in the sample irradiated with light, and outputs a particle signal corresponding to the particles;
an obtainer for obtaining a first pulse width that indicates a period of time during which the particle signal exceeds a first threshold value, a second pulse width that indicates a period of time during which the particle signal exceeds a second threshold value that is greater than the first threshold value, and sum of the second pulse widths with respect to each of particles;
a classifier for preparing a two-dimensional distribution drawing displaying a pathological cast area based on the first pulse width and the sum of the second pulse widths, wherein the pathological cast contains three or more particle-shaped contents; and
a display for displaying the prepared two-dimensional distribution drawing.

14. The particle classifying apparatus according to claim 13, wherein the light-receiving device receives fluorescent light from the particles, and the first and second pulse widths are pulse widths of the fluorescent light.

15. The particle classifying apparatus according to claim 13, wherein the light-receiving device receives scattered light from the particles, and the first and second pluse widths are pulse widths of the scattered light.

16. The particle classifying apparatus according to claim 13, wherein the two-dimensional distribution drawing displays a cast area.

17. The particle classified apparatus according to claim 13, wherein the two-dimensional distribution drawing displays a white blood cell area or an epithelial cell area.

* * * * *